United States Patent [19]

(12) United States Patent
Li et al.

(10) Patent No.: US 11,657,894 B2
(45) Date of Patent: May 23, 2023

(54) MEDIA, METHODS, AND SYSTEMS FOR PROTEIN DESIGN AND OPTIMIZATION

(71) Applicant: BASF SE, Ludwigshafen (DE)

(72) Inventors: Tong Li, San Diego, CA (US); Brian Standen, San Diego, CA (US); Dejan Caglic, San Diego, CA (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 17/772,976

(22) PCT Filed: Jul. 6, 2021

(86) PCT No.: PCT/IB2021/056049
§ 371 (c)(1),
(2) Date: Apr. 28, 2022

(87) PCT Pub. No.: WO2022/009092
PCT Pub. Date: Jan. 13, 2022

(65) Prior Publication Data
US 2023/0042150 A1 Feb. 9, 2023

Related U.S. Application Data

(60) Provisional application No. 63/048,414, filed on Jul. 6, 2020.

(51) Int. Cl.
*G16B 15/20* (2019.01)
*G06N 10/60* (2022.01)
(Continued)

(52) U.S. Cl.
CPC ............. *G16B 15/20* (2019.02); *G06N 10/60* (2022.01); *G16B 15/30* (2019.02); *G16B 40/20* (2019.02)

(58) Field of Classification Search
CPC ........ G16B 15/20; G16B 20/20; G16B 20/30; G16B 20/50; G16B 30/00; G16B 30/10;
(Continued)

(56) References Cited

U.S. PATENT DOCUMENTS 10,468,119 B2 * 11/2019 Fleishman ............. G16C 20/60
2005/0079579 A1 * 4/2005 Wei ........................ C07K 14/56
435/325

(Continued)

FOREIGN PATENT DOCUMENTS

WO WO-2020188114 A1 * 9/2020 ............... A01H 1/04
WO WO-2021094115 A1 * 5/2021 ............ A01M 1/026

OTHER PUBLICATIONS

Outeiral et al, "The Prospects of Quantum Computers in Computational Molecular Biology", Dec. 2018, IBM Research & Development, vol. 62 No. 6, pp. 6:1-6:20. (Year: 2018).*

(Continued)

*Primary Examiner* — Paulinho E Smith
(74) *Attorney, Agent, or Firm* — Marshall, Gerstein & Borun LLP; Randall G. Rueth

(57) ABSTRACT

Exemplary embodiments relate to a protein engineering pipeline configured to optimize or improve proteins for specified functions. The problem space of such a task can grow quickly based on the sequence of the protein being optimized and the functions for which the protein is being designed. The solutions described herein allow the problem space to be efficiently searched by applying a combination of a protein design pipeline and an evaluation procedure performed on a quantum computer. As a result, single or
(Continued)

multiple amino acid substitutions at a site of interest may be predicted in order to generate optimized protein variants.

16 Claims, 5 Drawing Sheets

(51) Int. Cl.
  *G16B 40/20* (2019.01)
  *G16B 15/30* (2019.01)
(58) Field of Classification Search
  CPC ........ G16B 30/20; G16B 35/00; G16B 35/10; G16B 35/20; G16B 40/00; G16B 40/20; G16B 40/30; G06N 10/60
  See application file for complete search history.

(56) References Cited

U.S. PATENT DOCUMENTS

2013/0324426 A1* 12/2013 Brevnova .............. G16B 35/00
  506/8
2022/0155298 A1* 5/2022 Heilmann ........ G01N 33/56961

OTHER PUBLICATIONS

Cao et al., "Potential of quantum computing for drug discovery", IBM Journal of Research and Development., vol. 62, No. 6, Nov. 1, 2018 (Nov. 1, 2018), pp. 6:1-6:20.
International Search Report and Written Opinion for Application No. PCT/IB2021/056049 dated Oct. 6, 2021.
Khan et al., "Current updates on computer aided protein modeling and designing", International Journal of Biological Macromolecules, Elsevier BV, NL, vol. 85, Dec. 28, 2015 (Dec. 28, 2015), pp. 48-62.
Mulligan et al., "Designing Peptides on a Quantum Computers", bioRxiv, Mar. 11, 2020 (Mar. 11, 2020), pp. 1-20, Retrieved from the Internet: URL:https://www.biorxiv.org/content/10.1101/752485v2.full.pdf [retrieved on Aug. 24, 2020].
Outeiral et al., "The prospects of quantum computing in computational molecular biology", arxiv.org, Cornell University Library, 201 Olin Library Cornell University Ithaca, NY 14853, May 26, 2020 (May 26, 2020).

* cited by examiner

MEDIA, METHODS, AND SYSTEMS FOR PROTEIN DESIGN AND OPTIMIZATION

CROSS-REFERENCE TO RELATED APPLICATIONS

The present application is a national stage application, filed under 35 U.S.C. § 371, of International Application No. PCT/IB2021/056049, filed Jul. 6, 2021 and entitled "Media, Methods, and Systems for Protein Design and Optimization," which claims priority to U.S. Provisional Patent Application No. 63/048,414, filed Jul. 6, 2020, entitled "Media, Methods, and Systems for Protein Design and Optimization," the entire disclosures of which are incorporated herein by reference in their entireties.

TECHNICAL FIELD

The present disclosure is directed to methods and systems for optimizing a protein according to a protein property, and specifically to utilizing quantum computing for protein optimization.

BACKGROUND

The process of designing a protein or DNA with particular characteristics (e.g. thermostability, solvent stability, expressibility, solubility, activity on a particular substrate) or to perform a particular protein function is an important but highly complex computational problem. Protein design may start with an existing initial protein to be improved (although in some cases completely new, i.e. de novo designed, protein structures are used as a starting point). The initial protein is then modified with the goal of having the modified protein exhibit improved or new characteristics or a new or better ability to perform the specified function as compared to the initial protein.

A protein is made up a combination of twenty naturally occurring amino acids, each having a unique side chain. Different sidechains may have different effects on the protein's characteristics or ability to perform a specified function. There may be many different positions within a protein's amino acid sequence that could be adjusted; a typical protein design task might involve evaluating changes to tens or even hundreds of positions.

Further complicating the problem, sidechains may be arranged in different possible discrete conformations (referred to as "rotamers"). There might be dozens to thousands of different rotamers possible at each position.

Accordingly, an exhaustive search of the different possible combinations of adjusted sequences, and their possible conformations, rapidly exceeds the capabilities of conventional computing systems. For reference, one would preferably like to test all of the available tens-to-hundreds of positions along the initial amino acid sequence with all available rotamers. Given the power available to conventional computers, typical searches are performed by testing approximately 3-5 positions using a library of preselected rotamers (although the number of positions may be increased if the rotamer libraries are small or filtered; generally one must choose between searching more positions, substitutions, or rotamers). In some cases, very powerful supercomputers may be capable of searching 6-7 positions with a limited number of rotamers.

Because classical computers cannot sample all states of conformations at once, heuristic methods have been developed to try combinations essentially at random. For example, conventional software has been developed that uses simulated annealing-based heuristics to efficiently search the available sequence and rotamer space. Although this procedure is not guaranteed to converge to the global optimum, it does tend to find good solutions relatively quickly. Unfortunately, the sequence and rotamer space quickly grows too large for simulated annealing approaches as the number of designable positions or the number of rotamer possibilities at each position grows. Thus, large protein design tasks can rapidly become intractable.

Consequently, the protein design process can be overly reliant on subjectivity and luck. The protein designer must apply their own knowledge of which protein locations are best manipulated in order to achieve the desired results, and which rotamer libraries to apply at those positions; two different protein designers may have different opinions as to which positions and libraries to try. Further choices may be made with respect to which scoring function to use to calculate modified properties, which set of substitutions to consider, and which rotamer substitutions to test. When applying simulated annealing on top of these design choices, only a subset of those subjectively-chosen combinations are tested at random.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Terms

Figure 1:
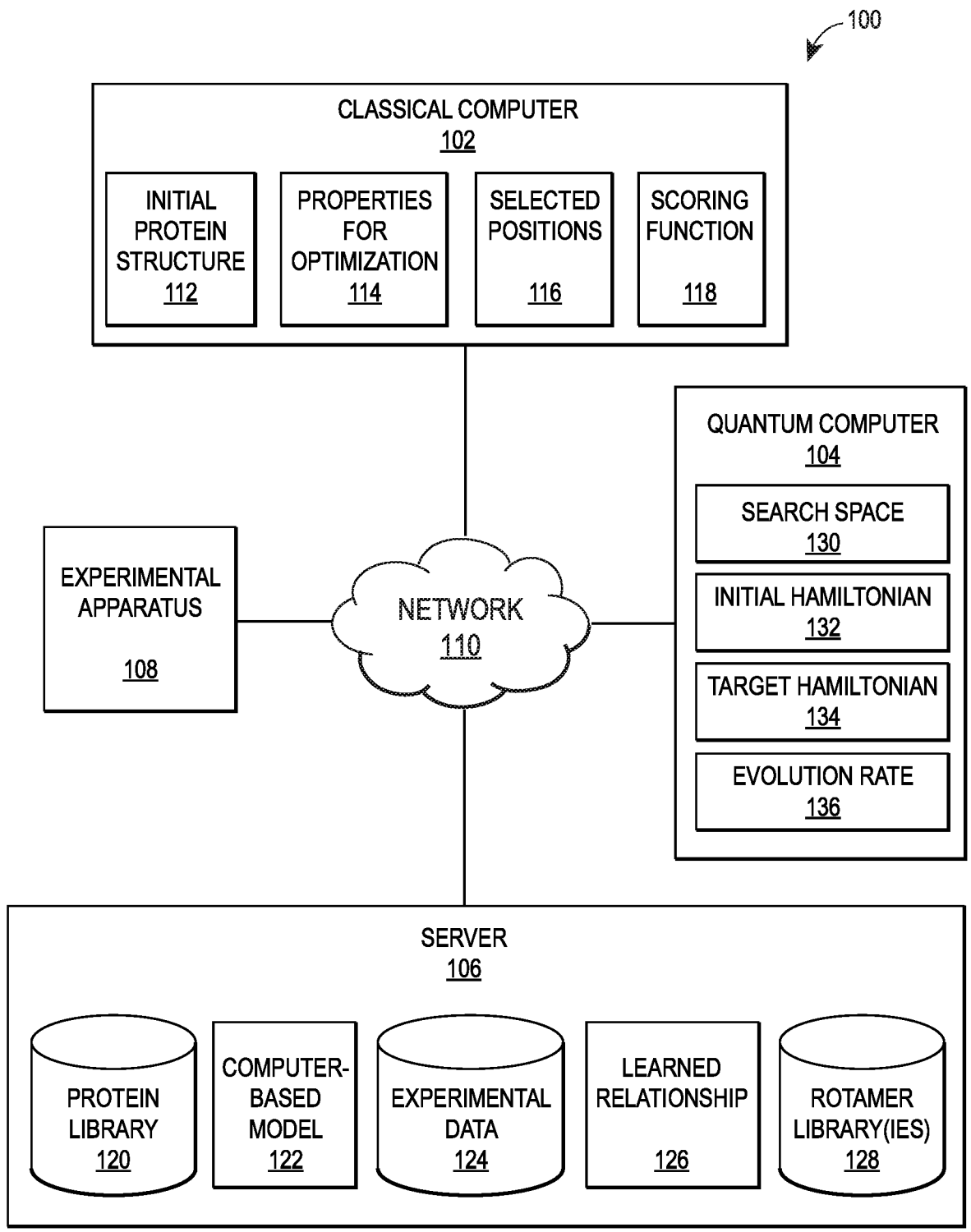
FIG. 1 illustrates an environment 100 suitable for practicing exemplary embodiments.

As used herein:

An "amino acid" may refer to one of the twenty naturally occurring amino acids and residues and/or modified, unnatural, or unusual amino acids and residues.

"Artificial intelligence" may refer to a computational structure that behaves in a manner similar to, or exhibits properties of, human intelligence.

An "association" between a configuration of an optimized protein and a protein property may refer to a qualitative or quantitative mapping between the protein and the property that represents the degree to which the protein exhibits the property.

A "binding partner" may refer to a protein molecule that interacts with another protein molecule via physical contact of high specificity, typically involving electrostatic forces and/or hydrophobic effects.

A "classical computing system" may refer to any computing system that performs computation without relying on quantum interference or quantum superposition to perform the computation.

A "computer-based model" may refer to a mathematical representation of a system that can be evaluated or simulated in order to predict the behavior of the system under specified conditions.

An "experimental apparatus" may refer to a device configured to measure one or more properties of a protein.

A "DNA sequence encoding a protein" may refer to genetic code that can be used to define the structure or configuration of a protein.

"Experimental data" may refer to data generated by an experimental apparatus, especially data that measures properties of a protein such as properties targeted for optimization. Further, the term "experimental" may be referred to synonymously herein as "empirical," such as in experimental data may also be referred to as "empirical data" and determining something empirically may be considered to be determining something experimentally.

"Machine learning" may refer to a class of computer algorithms that allow the computer to improve its ability to perform a task through experience.

A "modification" of a position may refer to a change in an amino acid occurring at a given position. A modification may include a substitution of one amino acid for another, an insertion of an amino acid into the protein structure, or a deletion of an amino acid that exists at a position in the protein structure. A modification may be a point mutation (i.e., a change in one of the above properties considered in isolation) or may be a combination of modifications that are considered as a group.

A "mutation" may refer to a change of amino acid in a protein sequence.

An "optimized protein" may refer to a protein that results from modifying a starting protein structure with the goal that the optimized protein exhibits a protein property for optimization to a high degree. In some cases, the base protein structure may exhibit the protein property to a first degree, whereas the optimized protein exhibits the protein property to a second degree greater than the first degree. In some cases, the optimized protein may exhibit the protein property to a degree greater than other proteins in a search space, although this is not a requirement and a protein may be considered optimized if it represents only an improvement or local maximum in the search space.

A "position" on a protein structure may refer to a location of an amino acid and/or an amino acid's associated side chain within the protein structure.

A "protein" may refer to a biomolecule consisting of one or more chains of amino acid residues.

A "protein configuration" may refer to a two- or three-dimensional protein structure, an amino acid sequence, a DNA sequence that encodes a protein, a catalytic domain, or one or more domains of a protein.

A "protein property for optimization" may refer to measurable characteristics that differ between different proteins. Such properties may include how well the protein performs a given function, the extent to which it exhibits a certain characteristic, or how well it binds to a given binding agent. Examples of protein properties for optimization include, but are not limited to: the stability of the protein in terms of thermostability, pH stability, solvent stability, stability to other excipients, and/or stability in application; expressibility; solubility; charge distribution; protein folding; activity; specificity in terms of bond, group, substrate, stereospecificity, and/or co-factor; reversibility; enzyme kinetics; substrate inhibition; product inhibition; resistance to protease degradation; gain-of-new function; the affinity of the protein to the binding agent; or the specificity of the protein binding to similar binding partners.

A "protein structure" may refer to a unique structure into which a protein naturally folds.

A "quantum annealing function" may refer to an algorithm configured to find a minimum of an objective function over a set of candidate states defined by a search space by leveraging quantum tunneling between states.

A "quantum computing algorithm" may refer to an algorithm operable on a quantum computing system that makes use of quantum properties of one or more particles in order to perform a computation. A quantum computing algorithm may or may not be faster or more efficient than a comparable classical computing algorithm.

"Quantum computing hardware" may refer to properties of a quantum computing system that define how much quantum processing power a quantum computer possesses, how much information the quantum computer can store or process, and/or how quickly, efficiently, accurately, or frequently the quantum computer can make use of that processing power and/or storage capacity. Some examples of measurements of quantum computing hardware include the number of qubits that can be manipulated by the quantum computer, the configuration or architecture of the qubits, the error rate in the hardware, the amount of noise in the hardware, the decoherence time of the qubits, and other features that may limit the availability or usability of the quantum hardware.

A "quantum computing system" may refer to a computing system that uses quantum properties of particles in order to perform quantum computations. Quantum computing systems may leverage phenomenon such as quantum superposition and/or entanglement in order to probabilistically evaluate multiple solutions to a problem at the same time.

A "quantum control signal" may refer to a classical input configured to be provided to a quantum computer to guide the quantum computer in performing a quantum computing algorithm. The quantum control signal may include input data that the quantum computing algorithm operates upon, may define a search space to be searched by the quantum computing algorithm, may provide limits on the operation of the quantum computing algorithm (e.g., values not to be searched, variables that must be considered or changed in combination with each other, etc.), may provide an initial protein structure to be modified, may designate one or more rotamer libraries to be considered, or may identify one or more positions in the protein structure to be considered for modification, among other possibilities.

A "quantum paradigm" may refer to a quantum process or algorithm and any corresponding quantum hardware capable of performing the quantum algorithm. The quantum paradigm may include one or more quantum computing systems, quantum control signals, quantum computing algorithms, and quantum computer hardware as required to accomplish the quantum paradigm.

A "rotamer" may refer to any of a number of isomers of a molecule that can be interconverted by rotation of part of the molecule around a particular bond.

A "rotamer library" may refer to a data structure defining a set of rotamers available to be used for a given purpose (such as modifying a protein). A rotamer may describe rotamer properties, such as rotamer torsion values and probabilities.

A "scoring function" may refer to a mathematical equation or relationship that maps a given input, such as a protein structure, to a score representing how well the input conforms to a predefined criteria (such as how much the protein structure exhibits the protein property for optimization).

A "search space" may refer to a domain of a function to be optimized. It may include all possible solutions to a search problem, or may be constrained to include only a limited subset of all possible solutions. Each point in the search space may correspond to a configuration (e.g., a protein structure) that serves as a candidate solution to an optimization problem. Points of a search space may also be referred to as "states" of the search space.

Embodiments

As noted above, conventional computing systems cannot search an entire problem search space for a given protein design process. However, quantum computers are capable of solving a problem of this type because quantum computers can evaluate multiple, and possibly all, options within a problem search space at the same time.

In some exemplary embodiments, a search space is defined by all possible amino acid substitutions, and the combination of the different possible rotamers for those amino acids, that may be used at each position along a protein structure. The amino acids capable of being substituted may include all 20 natural amino acids, as well as unnatural, modified, and unusual amino acids and residues. The search space is searched by exploiting quantum annealing, digital annealing, quantum-inspired algorithms, gate-based quantum algorithms, quantum simulation, and quantum-inspired optimizations to identify very low energy states yielding optimal protein sequences having improved properties and desired characteristics. It is noted, however, that exemplary embodiments are not limited to a particular quantum algorithm such as quantum annealing, but could also be applied with other suitable quantum algorithms, quantum-inspired algorithms, and quantum-inspired optimizations (i.e., the Quantum Approximate Optimization Algorithm (QAOA), Grover Adaptive Search (GAS), adiabatic quantum computing, quantum least squares fitting, quantum semidefinite programming, quantum combinatorial optimization, quantum-inspired stochastic regressions, a quantum-inspired evolutionary algorithm (QIEA), quantum Monte Carlo quantum annealing, simulated quantum annealing, quantum simulated annealing, or by evaluating protein candidates through quantum simulation with a variational quantum eigensolver). For simplicity, the term "quantum-based search" may be used herein to refer to any quantum algorithm, quantum-inspired algorithm, quantum-inspired optimization, or any hybrid quantum-classical algorithm or optimization.

The main advantages or leveraging quantum computing over classical solvers and computer systems are in terms of scaling and sampling. While classical solvers rely on sampling one state at a time, quantum annealing can consider multiple states of a search space, and therefore, may determine multiple possible solutions simultaneously via a superposition representation of the states encoded into a single Hamiltonian. This allows for a more efficient sampling method of sparse energy landscapes in a search space and may scale much better as problems and search spaces increase in size as compared to classical methods.

Initial results suggest that, even with the limited quantum computing hardware available today, a quantum based search of a search space can be performed with the search space including significantly more positions of an initial amino acid sequence and using all possible rotamers, as compared to classical optimizations and algorithms. This demonstrates a significant improvement over what can be accomplished using classical hardware.

As quantum hardware improves, the protein design pipeline described herein may be used to efficiently search an entire possible search space including all possible positions of an amino acid sequence, and all possible rotamer combinations. Even with current capabilities of quantum computers and quantum computing devices, however, pipeline quantum search still provides a way to search a larger search space, with more positions on an amino acid sequence and larger libraries of rotamers, than a classical technique. Moreover, the quantum search may be carried out more efficient with both time and computational resources because the pipeline of a quantum search focuses on the positions of the protein structure, and/or the specific rotamers to be considered, that are most likely to yield desired results. Classical systems typically rely on subjective design choices to determine a starting point, or determine a subset of a search space to search. Alternatively, a quantum search can further identify candidate states of a search space based on modeling and empirical or experimental data that can be improved over time as more empirical or experimental data is collected and as more optimizations and iterations of the quantum search are performed.

In some embodiments, the allowable complexity of the search problem (i.e., the size of a search space, the variables being considered, etc.) may be determined based on the hardware available to perform the search. For example, the search space may be defined by the number of amino acid positions of a protein and rotamers under consideration. Given a certain level of quantum computing hardware, it may be known that a search space of a certain size can be searched. Accordingly, a maximum complexity of the search problem may be identified (e.g., by calculating a value representing a complexity threshold, over which the hardware will not be able to efficiently perform the search), and used to set limits on the number of positions and rotamers that may be searched. The maximum complexity identified may further guide the operator in selecting an appropriate region on a protein, resulting in a smaller search space and more efficient search of the search space. In some embodiments, users may use the calculated complexity threshold to trade off certain elements of complexity for others in order to stay within the complexity limit, such as by searching a larger number of positions with a smaller rotamer library, or vice versa.

In some embodiments, artificial intelligence/machine learning (AI/ML) may be applied to learn relationships between a protein structure, positions of amino acids within the amino acid sequence of a protein, and rotamers, and/or protein characteristics or functionality. Information pertaining to a protein structure, amino acids, rotamers, protein characteristics, and protein functionalities may be learned from models, literature, and/or empirical/experimental data, and may inform the decision of which protein structure to use as an initial structure for performing an optimization, which structural positions to consider as candidates for changes, which subset of amino acid substitutions, and which rotamers to consider in those positions. This may be summarized as the information obtained from models, literature, and/or empirical/experimental data may be used to determine a starting, initial protein structure, and a search space to perform a quantum search and to determine an optimized protein structure according to desired protein characteristics and/or properties. In some cases, the data obtained indicative of relationships of the protein structures, amino acids, rotamers, etc., may inform a decision of which structures, positions, amino acid substitutions and/or rotamers should not be considered—for example, if it is known that changing the side-chain at a particular position along the protein structure results in only a very limited improvement in the desired characteristics, or has an otherwise negative effect, then that specific side chain substitution may be removed or omitted from a given search space.

In some embodiments, the understanding of the above-noted relationships between protein structures, amino acids, rotamers, etc. may be further improved in a feedback loop. First, for given desired characteristics or functionalities of a protein, a system may recommend structures, positions, amino acid substitutions, and/or rotamers for testing or synthesis based on historic experimental data or literature. An experimental pipeline may then be applied to identify one or more most-likely adjusted protein candidates that are deemed likely to improve the initial properties. For example, adjusted proteins may be fabricated and preliminary modifications to proteins may be performed to better understand and determine which positions in a protein structure or protein sequence are candidates for modification. Further, protein modifications may be performed in silico to determine candidate protein sequences, protein structures, and sequence modifications for performing optimization. Literature searching may also be used to determine candidate proteins and determine candidate locations for modification.

The adjusted protein candidates may be formulated and tested on experimental equipment in order to generate experimental data. The experimental data may then be analyzed by the AI/ML system to further improve the confidence level of the AI/ML system with respect to relationships between the protein structures, positions, amino acid sidechains, and rotamers and the characteristics/functionality of the protein. The characteristic or functionality of the protein may be used to define the optimized or improved properties of the protein. With this improved understanding of protein candidates and their properties and functionalities, the system may recommend different structures, positions, amino acid substitutions, or rotamers in future experiments, simulations, optimizations, and/or quantum searches.

FIG. 1 depicts an exemplary environment 100 suitable for implementing a protein design pipeline as described herein. The environment 100 may include a classical computer 102 configured to perform an initial setup of a search problem. The classical computer 104 may be supported by a server 106, in direct or indirect communication with the classical computer 102, in order to determine initial search parameters that guide the search, such as an initial protein structure, initial amino acids of the protein, the number of positions of a protein structure, and/or the number of rotamers to be included in the search space. Once the initial search parameters are established by the classical computer 102, the search parameters may be used to define an input for a quantum computer 104, which performs the quantum search and returns adjusted candidate proteins. The adjusted candidate proteins may be synthesized and tested by an experimental apparatus 108 to determine whether the adjusted proteins exhibit the predicted or desired characteristics. The candidate adjusted proteins may include one or more target initial proteins for optimization according to a desired protein property or characteristic.

In order to set up the search problem, the classical computer 102 may identify an initial protein structure 112 and/or initial protein sequence suitable for modification and/or a binding partner of interest. A suitable initial protein structure may relate for example to a structure with a protein property close to the desired property or characteristic. Such a determination of a suitable protein structure may be based on experimental data 124 or a computer-based model 122. For methods described herein, the structure of a protein may be represented in a number of ways, such as a two- or three-dimensional protein structure, an amino acid sequence, a DNA encoding polypeptide that encodes the protein, a catalytic domain, or one or more domains of an enzyme.

The initial protein structure 112 may be a structure selected from a protein library 120 stored on the server 106. Alternatively, the initial protein structure 112 may not be selected based on experimental data 124, and may be generated dynamically based on a computer-based model 122.

A candidate binding partner may be any suitable molecule for binding to a given protein. For example, it may be a protein, a nucleic acid such as DNA or RNA, a polysaccharide, a small molecule, or another polymer or other molecule. In some cases, no binding partner may be used, in which case the candidate protein may be optimized for function or characteristics in the absence of any binding partner.

The computer-based model 122 may predict an initial protein structure having one or more protein properties based on existing homolog structures, based directly de novo without a homologous structure, based on a binding partner of interest and existing experimental data 124, or based on any available learned relationships 126, as described in more detail below. In some embodiments, the protein of interest and one or more binding partners may be identified based on x-ray techniques, spectroscopy, crystallography, NMR, Cryo-EM, or other suitable techniques.

The classical computer 102 may further store properties for optimization 114. The properties for optimization 114 may include properties of the initial protein that the designer wishes to improve or characteristics of the initial protein that the designer would like to alter. For example, suitable properties for optimization 114 might include, the stability of the protein (e.g., thermostability, pH stability, solvent stability, stability to other excipients, stability in a specific application), expressibility, solubility, charge distribution, protein folding, activity, specificity (e.g., bond specificity, group specificity, substrate specificity, stereospecificity, or co-factor specificity), reversibility, enzyme kinetics, substrate inhibition, product inhibition, resistance to protease degradation, gain-of-new function, or the affinity of the protein to a binding agent or the specificity of the protein binding to similar binding partners.

The classical computer 102 may further store selected positions 126 along the protein structure 112 or protein sequence that are suitable for modification. The selected positions 116 might for example, include all possible positions along the protein structure 112 or protein sequence at which side-chains may be attached, or a subset of such positions determined by the computer-based model 122, learned relationships 126, and/or user input indicating positions along the protein structure 112 most likely to affect the desired properties for optimization 114. In some cases, some positions along the protein structure 112 or protein sequence may be flagged as critical (e.g., by the computer-based model 122, the learned relationships 126, a user input, etc.) such that the flagged positions should not be considered for the selected positions 116. For example, at positions known to have conserved, or catalytic residues, it may be understood that modifying an amino acid at that position will destroy the desired activity, function, or performance of the protein. Any positions flagged as critical may be filtered out of consideration, thus allowing the search space to be reduced. Alternatively, or in addition, positions may be flagged as more, or less, important for purposes of the search. For example, positions may be indicated that are known to have a major or minor impact on the desired protein function or characteristics as determined by modeling, AI/ML, etc.

Any flagged locations, such as locations flagged as critical, more important, or less important may be presented to a user on a user interface. For example, a graphical user interface may show a model of the protein being modified, and may highlight, flag, or otherwise visually distinguish locations on the model that are critical, more important, or less important to one or more protein functions and/or characteristics. In some embodiments, a user may select one or more of the identified locations of the model in order to receive more information about those locations (e.g., such as any information about protein characteristics or functions that are relevant to the selected locations, a degree to which modifying the selected location is likely to alter the characteristics or functions, experimental data in which the locations were tested with respect to the optimizable characteristics or functions, etc.). The described location flagging techniques may also be employed outside the realm of protein optimization, and may instead be used to highlight locations that are, or are not, important to certain protein functions and/or characteristics.

The classical computer 102 may further store a scoring function 118, providing (e.g.) a mapping of a given protein's structure to a score representing how well the protein performs with respect to the properties for optimization 114 or exhibits the target optimizable characteristics. For example, the scoring function 118 might be represented as a pairwise rotamer energy mapping that can be applied, or adapted, by the quantum computer 104 as a Hamiltonian. Candidate proteins may be evaluated by the quantum computer 104 against the scoring function 118 to determine which candidate proteins are optimal, and which proteins may be sub-optimal. In some embodiments, the scoring function might calculate a system energy value, such as delta delta G (DDG) to rank variants of a protein, although other types of scoring functions may also be used. In embodiments, the scoring function may be a statistical- or knowledge-based scoring function that is based on a studied interaction of molecules and bonds of a protein. The statistical- or knowledge-based scoring function may include a number of specific interactions that occur for a given protein sequence and protein structure (e.g., distances of rotamers, types of rotamers, types of amino acid, angle constraints, etc.).

The classical computer 102 may also select a set of rotamers to be considered at the selected positions 116. The rotamers may be a set of rotamers from a rotamer library 128 stored on the server 106. In some embodiments, the rotamer library made available for a particular search may be determined from a plurality of rotamer libraries based on the available quantum hardware, quantum algorithm, or a quantum paradigm for performing the quantum computation. For example, information about the hardware on the quantum computer 104 (e.g., the number of qubits, their arrangement into an architecture, their modalities, their coherence times, the noise level in the quantum computer 104, etc.), may allow the classical computer 102 and/or server 106 to calculate a complexity value representing a maximum complexity for the search space that can be handled by the quantum computer 104. One or more rotamer libraries made available for the search may be selected so that they do not increase the search space to the point where the complexity of the search space would exceed the calculated complexity value.

As more or fewer positions along the protein structure 112 are selected for the search space, the complexity score, and corresponding available rotamer libraries 128, may also be adjusted. The classical computer 102 may make information about the complexity available on a user interface, so that a protein designer (i.e., a user of the device) can see the trade-offs being made as they select positions for adjustment. If the protein designer wishes to make more rotamer libraries accessible for a given complexity of the problem and the available quantum hardware, the designer can choose to include fewer positions and/or a smaller subset of amino acid substitutions in the search space in order to reduce the complexity and to make more rotamer libraries available, or vice versa.

The selected positions 116, the selected subset of amino acid substitutions and the selected set of rotamers of the available rotamer libraries 128 define the search space 130 to be considered by the quantum computer. A representation of the search space 130 and the scoring function 118 may be provided to the quantum computer 104 for evaluation.

In a quantum annealing paradigm, the quantum computer 104 may select an initial Hamiltonian 132 and the quantum computer 104 may configure itself according to the initial Hamiltonian 132. Typically, the initial Hamiltonian 132 is selected to have a configuration of the quantum computer 104 that is relatively simple to achieve, given the quantum computer's hardware configuration. The initial Hamiltonian 132 is slowly evolved into a representation of the problem's target Hamiltonian 134, which is generally a representation of, and defined by, the scoring function 118.

An important aspect of the quantum annealing algorithm is the evolution rate 136, which defines how quickly the initial Hamiltonian 132 is allowed to evolve into the target Hamiltonian 134. If the evolution rate 136 is too fast, the evolving Hamiltonian will leave its ground state and may not be able to settle back to the ground state in order to evolve into the target Hamiltonian 134. However, if the evolution rate 136 is too slow, the time-to-solution is increased, which may also prevent the Hamiltonian from ever evolving to within a desired range of the target Hamiltonian 134. Additionally, a slow evolution rate 136 may result in a failed optimization if the qubit modality selected has a relatively low coherence time, or has high level of noise, which may cause the quantum search system to degrade into incoherence before a solution can be achieved. Thus, the evolution rate 136 should be selected on a case-by-case basis depending on the nature of the target Hamiltonian 134 and the fidelity of the quantum hardware available. In some cases, the evolution rate 136 may be allowed to vary over the course of the search, adjusting itself to become slower as the system approaches a transition point of the energy gap as the energy gap between the ground state and a lowest excited state decreases below a threshold. The evolution rate 136 may increase during other parts of the search when the energy gap between the ground state and first excited state is greater than the threshold.

After the initial Hamiltonian 132 is evolved into the target Hamiltonian 134, the state of the quantum computer 104 may be measured. The measurement will generally reflect a particular arrangement of the states of the qubits (i.e., each qubit is measured to be either a 0 or a 1) whose configuration defines a protein structure. The resulting structure may represent an optimized (or, at least, an improved) version of the protein being searched for. In some embodiments, the quantum search algorithm may be run multiple times in order to screen out false positives and/or to provide multiple candidate proteins for consideration.

Figure 3:
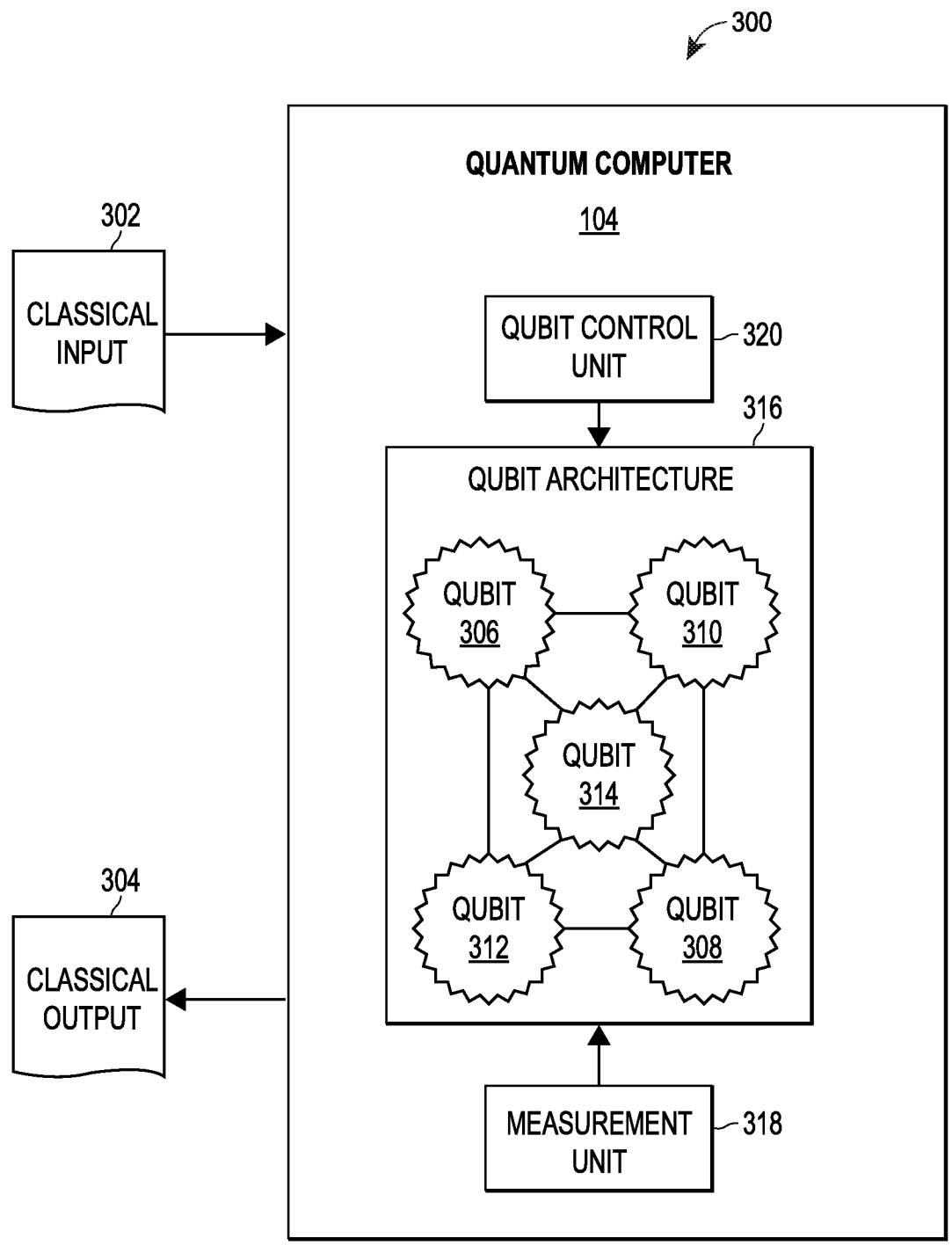
FIG. 3 illustrates an exemplary quantum computer suitable for use with one embodiment.
Figure 4:
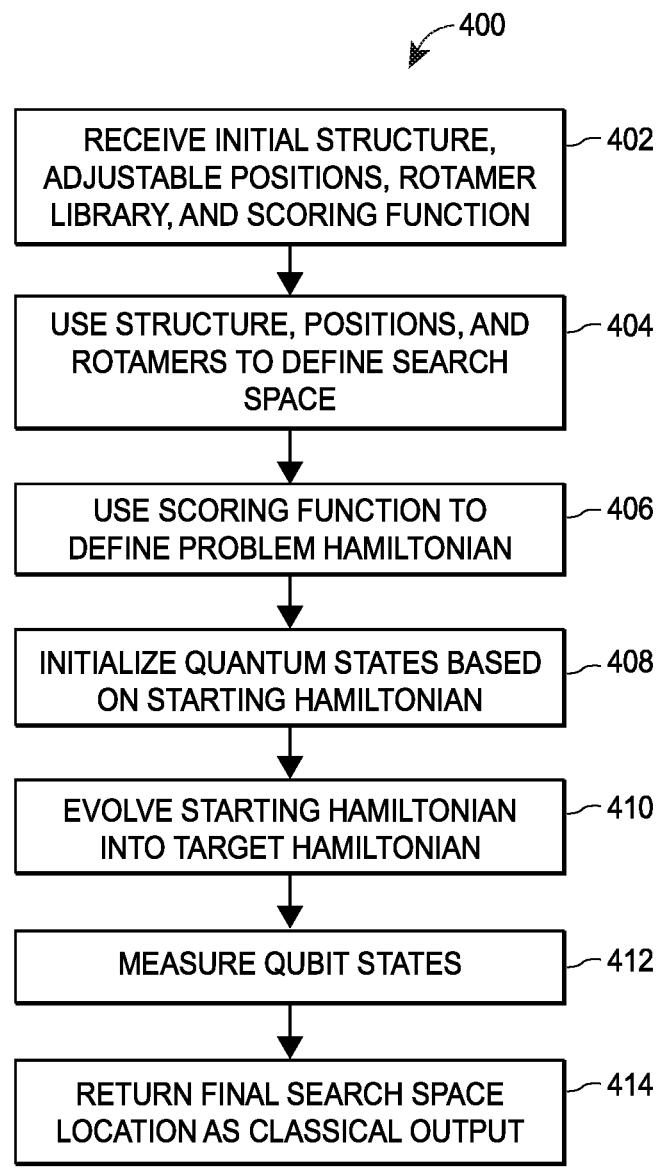
FIG. 4 illustrates an exemplary quantum algorithm in accordance with one embodiment.

The quantum computer is discussed in more detail herein in reference to FIG. 3, and an embodiment of a quantum algorithm is discussed in more detail in reference to FIG. 4. It should be noted that the above description is specific to one particular quantum computing paradigm (i.e., quantum annealing), but the present systems and methods are not limited to the particular implementation explicitly described. Instead, the described quantum annealing example is provided as an illustration only; it is contemplated that the protein design pipeline may be applied with other types of quantum algorithms, such as the Quantum Approximate Optimization Algorithm (QAOA) for gate-based quantum computing hardware. One of ordinary skill in the art will understand, in light of the teachings of the present disclosure, how to adjust the inputs from the classical computer 102 to accommodate other types of quantum algorithms and quantum computers 104.

After the quantum computer 104 provides one or more output candidate protein sequences for consideration, the experimental apparatus 108 may be used to test the candidate protein sequences to determine which of the output candidate protein sequences perform the best with respect to the properties for optimization 114. Testing the candidate protein sequences may generate data, which may be stored as experimental data 124 on the server 106. The experimental data 124 may provide insights as to which positions and which amino acid substitutions are more effective for tuning protein properties of interest, which rotamer libraries are more likely to affect those proteins, how changes to the rotamers in certain positions change the protein properties of interest, etc.

The server 106 may use the experimental data, potentially in conjunction with an AI/ML system, to build the computer-based model 122 and/or determine rules or learned relationships 126 between the protein structure, positions, and rotamers and the properties for optimization 114. This aspect of the pipeline is discussed in more detail in reference to FIG. 5.

The various components of the environment 100 may be connected together, or otherwise communicatively coupled, by a suitable network 110, such as the Internet, an intranet, direct wired or wireless connections, or another type of network.

Figure 2:
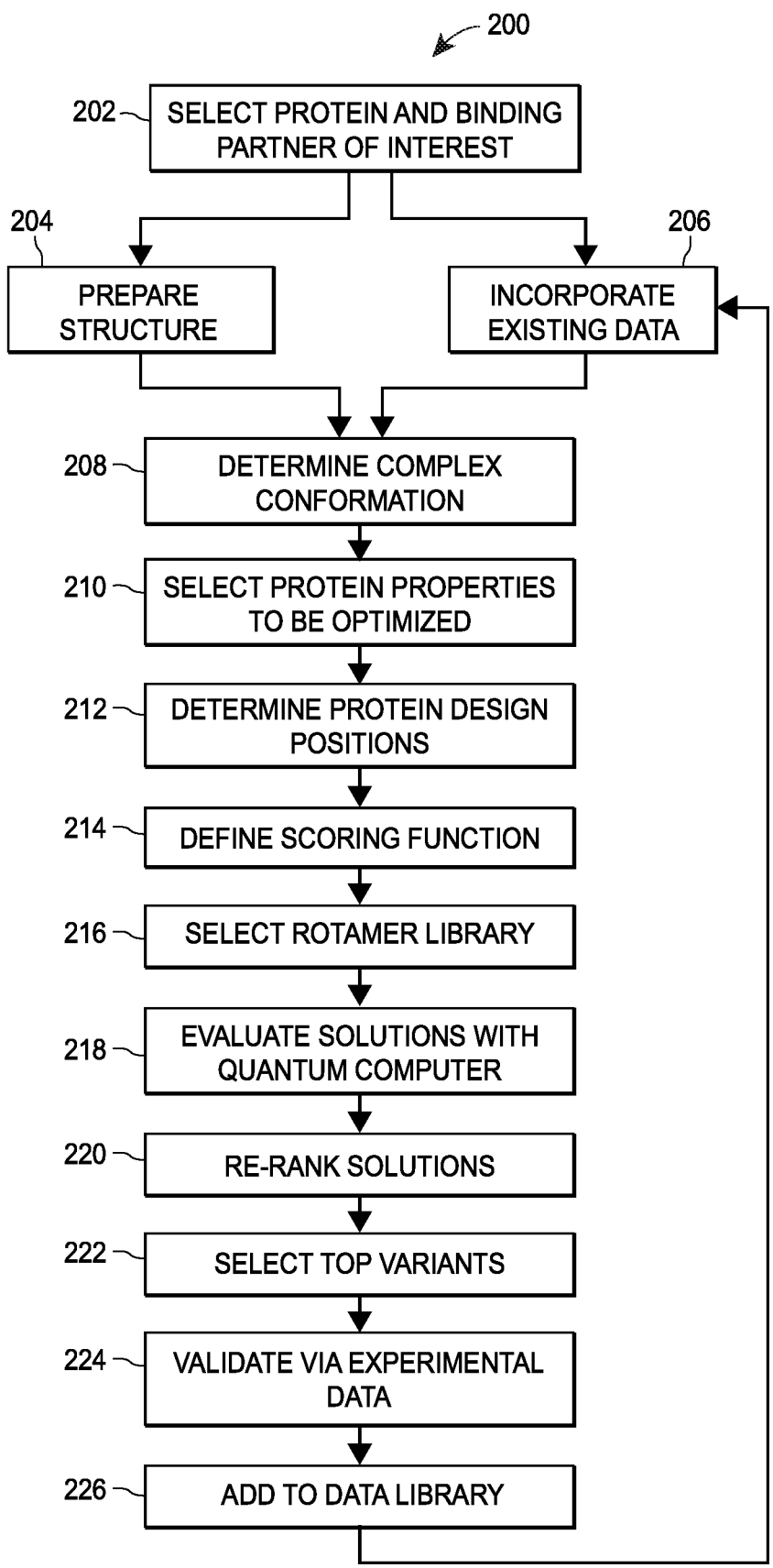
FIG. 2 is a flowchart depicting exemplary logic for implementing a protein design pipeline 200 in accordance with one embodiment.

FIG. 2 is a flowchart of a protein design pipeline 200 as described herein. The protein design pipeline 200 of FIG. 2 may be performed by the environment 100 of FIG. 1, and therefore, for illustrative purposes, aspects of the protein design pipeline 200 may be described with reference to elements of the environment 100. The protein design pipeline 200 begins at block 202, where the system selects an initial target protein structure, and/or a binding partner of interest (e.g., the initial protein structure 112 of FIG. 1). In some embodiments, the target protein structure is known; in others, the target protein structure is not known and must be determined at block 204 through computer-based modeling or mining existing data (e.g., the computer-based modeling 122 and experimental data 124). The system may simulate or model a number of different protein structures based on the binding partner of interest, and may select the protein structure or structures most likely to bind to the binding partner of interest. If multiple proteins are selected by the system as candidates, a list of the selected proteins may be presented to a user on an interface to allow the user to select one or more proteins for further evaluation. The candidate proteins may be displayed in a ranked list based on the modeling and simulation, where the rank of the proteins is based on the system's assessment of the protein's ability to bind to the binding partner of interest, if a binding partner is being used.

In some embodiments, the system may incorporate existing data into the computer-based modeling 122 or data for mining at block 206, which may include historic data from previous iterations of the protein design pipeline 200 that are generated as the protein design pipeline 200 is performed in a feedback loop. The existing or historic data may include a list of target protein structures from the protein library 120, information about the ability of a protein structure to bind to the binding partner of interest, complexity information about the protein structure which allows the system to select less complex protein structures when quantum hardware or quantum computing capacity is limited, protein performance, structure-function relationship, etc.

At block 208, the system may determine the complex conformation of the determined target protein structure with the binding partner of interest. At block 210, the system may select one or more protein properties to be optimized. The protein properties to be optimized may vary depending on the application, although in exemplary embodiments the specificity, activity, expressibility, solubility and/or the stability are optimized.

At block 212, the system may select positions along the initial protein sequence that are eligible to be changed (i.e., replace an amino acid at that position with a different candidate amino acid, delete or remove an amino acid, or add or insert an amino acid). The system may start with a list of all available positions in the protein structure, which may be predefined and stored in the protein library 120 or may be determined dynamically through modeling and simulation, among other possibilities. The list of available positions that are eligible for changing may be ranked based on an assessment by the classical computer 102 and/or server 106 as to which positions are most likely to have an effect on the protein properties to be optimized. The ranking may be determined based on modeling, the learned relationships 126, a search of available literature, etc., and may be affected in part with the assistance of AI/ML, further described in reference to FIG. 5.

In some cases, the system may allow a user to flag positions of the protein sequence that the user believes will be highly likely to affect the protein properties to be optimized. The flagged positions may be tested via modeling and/or experimental data to determine if they affect the protein properties as expected. If so, the resultant information from the modeling and/or experimental data is incorporated into the system's experimental data, models, and learned relationships for further use. In this way, the system can incorporate the subjective expert domain knowledge of a given user while still subjecting the domain knowledge to validation and verification through testing.

In some embodiments, the system may present a user interface allowing the user to select a set of amino acid substitutions or additions from among the 20 natural possibilities and/or unnatural amino acid substitutions. Alternatively, or in addition, the system may automatically select appropriate amino acid substitutions or additions. These substitutions or additions may be automatically selected or recommended to the user based on the results of the AI/ML algorithm, modeling, experimental data, or other suitable techniques for identifying which substitutions or additions are most likely to result in an improvement to the protein characteristics or functions that are being optimized. In some embodiments, the substitutions or additions may be ranked based on which substitutions or additions are most likely to result in an improvement to the protein characteristics or functions, and the substitutions and/or additions may be displayed in ranked order for user selection. Alternatively or in addition, only the top n, where n is a predetermined and/or customizable integer, results may be selected or recommended. Further, the system may limit the number of positions to modify, delete, or insert an amino acid, the number of rotamers, and the number of amino acids for limiting the scope of modifications of the protein depending on the quantum computing capacity and/or complexity.

In some cases, some positions and/or amino acid substitutions or deletions may be considered critical and may be "locked out" or prevented from being changed and therefore removed from a search space. The critical positions and/or critical amino acid substitutions or deletions may be determined based on experimental data, learned relationships, modeling, etc. Generally, critical positions and/or critical amino acid substitutions or deletions may include those positions/amino acids that cannot change without negatively affecting the folding, stability, solubility and/or performance of the protein, or positions for which changes will not significantly affect the protein properties to be optimized, etc. In some embodiments, positions may be locked out of changes when observations of homologous sequences from other tests have indicated that a change in a given position is unlikely to positively impact the target characteristic or function. To this end, information from evolutionary data and/or data from experimental databases may be used in order to determine which positions to lock out of a search space. Critical/locked out positions, critical amino acid substitutions, and/or deletions may be filtered out of the list of positions/substitutions/deletions eligible to be changed before the list or positions/substitutions/deletions is presented to the user, or the critical positions, critical amino acid substitutions, and/or deletions may be visually distinguished in the list so that the user can select them for changes if they want, with the understanding that the system considers these positions to be critical.

In some embodiments, the system may use the selected positions, amino acid substitutions, and/or deletions to calculate a complexity score, as described above. The complexity score may initially represent the complexity of the search space if all available rotamers are tested. If the complexity exceeds the hardware capabilities of the quantum computer 104, the system may programmatically exclude some rotamer libraries from consideration, or may allow a user to select which positions, amino acid substitutions, amino acid deletions, or rotamer libraries will or will not be considered for the search space. The user may override a programmatic selection of rotamer libraries to swap certain libraries for others. When selecting rotamer libraries for consideration, the system may weigh the complexity added by a selected rotamer library, as determined by the amount of increase to the complexity score if the rotamer library is included, against the likelihood that the rotamer library includes rotamers that will have a significant effect on the protein properties to be optimized.

At block 214, the system may define a scoring function that optimizes the protein properties identified in block 210. The scoring function may accept measured values for the protein properties as input and may output a calculated score that reflects how well those values meet certain scoring criteria. The protein properties may be weighted by the scoring function so that certain properties are weighted more than others or so that improvements to certain properties are weighted more than improvements to others. In some embodiments, the scoring function may have weight values that vary during an optimization or process so as to result in improvements to certain properties within selected ranges. For instance, initial improvements to the properties may be weighted heavily to encourage the property to reach a certain minimum threshold value. Above that minimum threshold value, improvements to the properties may be given less weight, so that other properties can be prioritized. Multiple thresholds or a continuum of weights may be defined so that trade-offs in improvements to different properties of interest can be made. Moreover, the scoring function may consider an associated cost of achieving an improvement to a protein property; the scoring function may weigh the improvement against the cost so that high-cost low-value improvements are not given a high priority.

At block 216, the system may select one or more rotamer libraries to be included in the search. As noted above, the change in complexity of the search space that results from including a rotamer library may be used to exclude rotamer libraries from consideration, or to force the user to decrease the number of positions and/or amino acid modifications under consideration. Conversely, if all desired rotamer libraries have been included or excluded and the complexity score indicates that the quantum hardware remains capable of performing the search efficiently, then the system may flag for the user that additional positions and/or amino acid modifications may be considered. This allows the user to increase the number of positions and/or amino acid modifications searched in the search space.

In some embodiments, a rotamer score may be calculated for each rotamer library based on the likelihood that the rotamers of the library will affect the protein properties to be optimized (e.g., based on modeling, experimental data, learned relationships, literature, etc.). The rotamer libraries may be arranged in a ranked order based on the rotamer score. Rotamer libraries having scores below a predetermined threshold may be excluded from consideration, and the complexity score may be updated to reflect the excluded libraries. In some embodiments, rotamer libraries may be excluded dynamically as the user selects more or fewer positions and/or amino acid modifications for consideration. For example, as the user incorporates more positions and/or amino acid modifications, the rotamer libraries having the lowest scores in the list may be successively excluded until the calculated complexity score is within the capabilities of the quantum computer 104. If the number of positions and/or amino acid modifications are reduced, rotamer libraries may be added back into the search space in an order based on the score of the rotamer library, so that more relevant rotamer libraries are added back in first. Thus, the protein design pipeline 200 may iterate between block 212 and block 216 as the positions, amino acid modifications and rotamer libraries are dynamically adjusted in view of each other.

At any point, the user may manually select one or more rotamer libraries for inclusion, based on their own domain knowledge about the problem or the properties of the protein being optimized. If the user selects a rotamer library for inclusion, the system may evaluate the rotamer library during the protein design process to determine if the rotamer score calculated for the rotamer library needs to be adjusted. For example, if the system determined that a given rotamer library was unlikely to affect the protein properties to be optimized, but the user overrode the exclusion of the library and the quantum algorithm determined that a rotamer from the library was a good candidate for the adjusted protein, then this information may be reflected in the experimental data 124 and may be used to adjust the computer-based model 122 and/or the learned relationships 126 for future optimizations and future iterations of the protein design pipeline 200. Accordingly, when the rotamer score is next calculated for the same rotamer for a same or similar optimization problem, the score may be higher than it was previously, making it more likely that the rotamer library will be included for consideration in the search space.

When a final selection of the positions, amino acid modifications and rotamer libraries is made, these selections may be used to define a search space for the protein optimization problem. The search space may represent a multidimensional encoding of all the different possible combinations of positions, amino acid modifications and rotamers, given the selections made at block 212 and block 216. At block 218, the system may access the conformed protein/binding partner from block 208, flag the positions identified at block 212 on the conformed protein, and provide the conformed protein/binding partner, the flagged protein positions, the scoring function from block 214, and the search space to the quantum computer 104. The quantum computer may evaluate these inputs using quantum algorithms, such as simulated quantum annealing, digital annealing, adiabatic quantum computing, Quantum Approximate Optimization Algorithm (QAOA), Grover Adaptive Search (GAS), gate-based quantum algorithms, quantum-inspired algorithms, or any other suitable quantum algorithm. A particular example employing quantum annealing is described in reference to FIG. 4.

With each execution of the quantum algorithm, the quantum computer 104 may select a mutated protein of the initial protein/binding partner of interest as a candidate for the optimized protein. The quantum algorithm may be executed multiple times to select multiple candidates as the optimized protein. In some embodiments, a same optimized protein candidate may be identified on multiple runs of the quantum algorithm, which may indicate an increased likelihood that the thus-identified candidate represents a global minimum, representing a sufficiently optimized protein. Based on the results of the runs of the quantum algorithm, the system may present a ranked list of candidate proteins (e.g., ranked in an order based on the number of times that the candidate proteins were identified by the quantum algorithm and/or based on the candidate protein's score as determined by the scoring function). The user may select one or more of the candidate proteins as proteins of interest for testing and validation; in other embodiments in which the protein is being optimized at a DNA level, then the user may be presented with, and may select, DNA sequences to select the candidate optimized protein.

Optionally, protein variants of interest may be re-ranked using quantum or classical algorithms at block 220. For example, after a quantum algorithm generates a short list of candidate proteins of interest for the optimized protein using a given scoring function, that short list may be re-ranked on classical hardware using a different scoring function. This re-ranking allows the most promising candidates to be selected by the quantum computer, and then further refined using classical computing techniques. Alternatively, a list of protein variants may be re-ranked on a quantum computer using a different scoring function. In another embodiment, classical hardware might re-rank the candidates using the same scoring function as applied by the quantum computer. In these embodiments, the classical computer may validate that the quantum ranking was performed as expected. Further, a list of proteins may be ranked, and re-ranked any number of times, with each re-ranking being performed by a quantum paradigm or a classical algorithm. As such, the list of proteins may be re-ranked and culled multiple times to determine one or more optimized protein sequences and/or structures.

Re-ranking of the protein variants may be performed multiple times in series using one or more different quantum paradigms and/or classical paradigms. For example, a first ranking of protein variants may be determined using quantum annealing, the top n ranked protein variants may then be passed to a second quantum computing system and further re-ranked using a different quantum computing paradigm such as by digital annealing or another paradigm. Further, different quantum and/or classical paradigms and algorithms may be used throughout the optimization process during different iterations of the optimization process until an optimized protein sequence and/or structure is determined having desired properties thereof.

At block 222, the system may select the top protein variant or the n top protein variants, where n is a predetermined integer, as candidate proteins. The top protein variants may be selected based on their rank as determined in blocks 218-220 and/or based on the score determined by the scoring function. At block 224, the selected candidate proteins may be tested by suitable experimental apparatuses. The testing may focus on the performance of the candidate proteins with respect to the properties to be optimized identified in block 210. However, the testing need not be limited to these properties, and other properties may also be tested at block 224. Based on the test results, experimental data may be generated. The experimental data may be added to a data library at block 224, and then subjected to AI/ML as described in more detail in reference to FIG. 5. This may result in an increased understanding of which positions and amino acid modifications are considered to be important or not important, which rotamer libraries are likely to affect which protein properties, which changes to the protein structure affect which properties, etc. This information may be fed back into the pipeline at block 206 so that future optimization problems can benefit from the information and improved insight.

Although the protein design pipeline 200 has been presented as a unified whole, it is noted that each block of the protein design pipeline 200 may be performed separately or in combination with a limited subset of other blocks in order to achieve specific advantages. For instance, although a quantum algorithm may allow a larger search space to be considered, it is contemplated that blocks 202-216 and 220-226 could be applied separately in a fully classical or hybrid quantum-classical context. To take block 212 as but one example, selecting the protein design positions, amino acid modifications, and rotamers is a problem applicable to protein design and optimization in general, and need not be employed solely in the context of performing optimization using a quantum computer. Similarly, the above-described complexity score could be applied to evaluate whether a classical computer was capable of efficiently searching a specified search space, allowing positions, amino acid modifications, and rotamer libraries to be selected so as to best utilize available classical hardware. Moreover, the use of AI/ML in blocks 222-226 to improve the understanding of the relationship between changes to a protein and the resulting improvement in specified protein properties has many applications in protein design and other fields.

FIG. 3 is a block diagram illustrating an exemplary quantum computing environment 300. The quantum computing environment 300 includes a quantum computer 104, which receives a classical input 302, performs a quantum algorithm based on the classical input 302, and generates a classical output 304. The classical output 304 may be based on a measurement of the state of the quantum computer 104 after the quantum computer 104 has performed the quantum algorithm.

According to one embodiment, the classical input 302 may include a protein having a protein structure with indicated positions of the protein structure that are subject to change. The classical input 302 may include a portion of a protein, such as an isolated binding site or pocket or a protein domain. Further, the classical input 302 may include a scoring function that is used to optimize desired properties of the protein. The classical input 302 may optionally include an identification of one or more rotamer libraries including rotamers that can be added to the flagged portion of the protein or in the flagged positions; if no rotamer library is provided, then all available rotamers may be searched. The classical input 302 may optionally include an identification of amino acid modifications that can be placed in the indicated positions or added to or removed from the portion of the protein; if no amino acid modifications are provided, then all available modifications may be searched. The identification may be in the form, for example, of a table of allowed modifications. In any embodiments, the classical input 302 may provide the quantum computer 104 with initial parameters (e.g., an initial protein structure and/or binding partner) and a search space for performing optimization of a property or characteristic of the protein.

The classical input 302 is used to encode the problem to be solved in the hardware of the quantum computer 104. Generally, a quantum computer 104 includes a number of qubits 306-314. Although FIG. 3 depicts only five qubits in a particular arrangement, it is understood that quantum computers may be designed with more or fewer qubits in different configurations.

The qubits 306-314 may be physically manifested in a number of different ways referred to as qubit modalities. Each different modality has different advantages and disadvantages with regards to ease of manufacturing, ease of use, error rate and coherence time, repeatability of results, etc. The above-described protein design pipeline 200 is generally applicable across a wide range of qubit modalities.

The qubits 306-314 may be arranged in a particular qubit architecture 316, which defines the interconnections between qubits. In quantum algorithms, a first qubit needs a communication pathway to a second qubit in order to have an effect on, or be affected by, the second qubit. These communication pathways are important in implementing certain quantum logic gates. However, given the constraints on quantum computers, particularly with regards to the topology of the qubits of the quantum computer, not every qubit is capable of addressing every other qubit. Thus, a specific qubit architecture 316 may limit the types of algorithms that can be run and the types of problems that can be solved. Generally, qubits are arranged into relatively small groups having a certain internal architecture, and the groups of qubits are connected to other qubit groups via external connections. One example of a qubit architecture 316 is the Pegasus architecture used by D-Wave Systems, Inc. of Burnaby, British Columbia. It is contemplated that the above-described protein design pipeline 200 may be used with any known qubit architecture 316 suitable for performing optimization and search problems.

The quantum computer 104 can be a general-purpose quantum computer, in which the states of the qubits 306-4314 are manipulated by universal logic gates capable of implementing any known quantum algorithm. However, the protein design pipeline 200 is also suitable for use with special-purpose quantum computers, such as computers specifically configured to perform quantum annealing or digital annealing. An example of such a special-purpose quantum computer are the D-Wave One, D-Wave Two, D-Wave 2X, D-Wave 2000Q, and D-Wave Advantage quantum annealing computers from D-Wave Systems, Inc. of Burnaby, British Columbia, and digital annealers, for example, as developed by Fujitsu.

When a quantum algorithm is executed, the qubits 306-314 are generally initialized into a starting state (e.g., based on the initial Hamiltonian 132) and are then manipulated according to the quantum algorithm being performed. In order to change the state of each qubit, a hardware qubit control unit 320 is provided. The specific qubit control unit 320 used may depend on the modality of the qubits 306-314 being manipulated. For example, superconducting qubits are generally addressed with microwaves provided by a microwave source employed as the qubit control unit 320, whereas trapped ions may be addressed using microwaves or optical systems such as lasers implemented as the qubit control unit 320. In any embodiment, the qubit control unit 320 includes hardware for manipulating the state of each of the qubits 306-314.

In addition to a qubit control unit 320, the quantum computer 104 requires a way to read the states of the qubits in order to return an answer to the problem presented. For example, at the end of a quantum annealing process, the states of the qubits (i.e., 0 or 1) may be arranged according to the target Hamiltonian 134, and the states of the thus-arranged qubit states may represent the selections for each of the position/amino acid/rotamer combinations that represent the lowest-energy state discovered as the algorithm is run. The qubit states therefore represent a mutated protein that minimizes the cost function according to the current run of the quantum algorithm Thus, the state of the qubits 306-314 must be read in order to return the answer to the problem.

To that end, the quantum computer 104 may include a hardware measurement unit 318. In some implementations, qubits can be read using the same techniques by which they are controlled, allowing the qubit control unit 320 and the measurement unit 318 to be the same. In other embodiments, the qubit control unit 320 may differ from the measurement unit 318. Different types of measurement units are employed depending on the qubit modality, since different modalities may store information in different ways. For example, a superconducting qubit stores its state as a phase of the Josephson junction used to form the qubit; it might be read with a magnetometer or microwave resonator as the measurement unit 318. A trapped ion stores its quantum state in the arrangement of the ion's electrons, which emits photons when in a specified state and excited by a laser. The state of the trapped ion may be read by an optical measurement device such as a charge coupled device (CCD) that detects photons when the trapped ion is in one state, and does not receive photons when the trapped ion is in another state.

Based on the measurement performed by the measurement unit 318, after the quantum algorithm has been performed, the quantum computer 104 provides a classical output 304. The classical output 304 may include a mutated protein sequence with optimal rotamer orientations that the quantum computer 104 has determined is most likely, given the classical input 302, to improve the protein properties for optimization.

FIG. 4 is a flow diagram of an exemplary quantum algorithm 400 suitable for use with exemplary embodiments of the protein design pipeline 200 of FIG. 22. As noted above, the particular implementation described in reference to FIG. 4 involves a quantum annealing algorithm, although other quantum algorithms are also applicable to the protein design pipeline 200.

Referring simultaneously to FIGS. 4 and 1, at block 402, the quantum computer 104 may receive the initial protein structure 112 with a list of adjustable positions, or with positions flagged on the protein structure for changing of an amino acid at the flagged positions, from the classical computer 102. The quantum computer 104 may also receive a list of amino acid modifications, a rotamer library, and the scoring function.

At block 404, the structure, positions, amino acid modifications, and rotamer library may be used to define a search space. The search space may be a representation, such as a vector space or other appropriate embedding, of the various possible combinations of positions, amino acid modifications, and rotamers. In some embodiments, the search space may be defined by the classical computer 102 and provided to the quantum computer 104.

At block 406, the scoring function may be used to define a target Hamiltonian 134. Generally, the scoring function provides a mapping from any given point in the search space to a corresponding score, which may represent an energy state. A Hamiltonian similarly matches a given arrangement of states of particle into an energy state. Given the scoring function, a target Hamiltonian 134 may be constructed such that the Hamiltonian is in its highest energy state when the scoring function is at a maximum, and its lowest energy state when the scoring function is at a minimum. In some cases, a target Hamiltonian 134 may be known for a given scoring function, and in some cases an existing Hamiltonian may need to be modified or a new one determined. The particular target Hamiltonian 134 chosen will depend on the scoring function and the properties being optimized, and so the target Hamiltonian 134 will vary on a case-by-case basis.

In addition to the target Hamiltonian 134, an initial Hamiltonian 132 may also be chosen. The initial Hamiltonian 132 is the starting Hamiltonian that the quantum algorithm will slowly evolve into the target Hamiltonian 134. To that end, an initial Hamiltonian 132 with a known ground state (i.e., low energy state) is generally selected; it may also be selected so as to be easy to initialize the initial Hamiltonian 132 given the quantum hardware involved. At block 408, the quantum computer 104 initializes the quantum states of the qubits 306-312 according to the initial Hamiltonian 132. A suitable initial Hamiltonian 132 may be one in which all qubits are co-aligned with a large, transverse X-field applied to all qubits. In embodiments, the X-field may be an applied magnetic, or electric, field in a direction that when applied to the qubits initializes the qubits into a ground state of the initial Hamiltonian 132. In a specific example, a suitable initial Hamiltonian 132 may be one in which all qubits are initialized in a superposition state of 0 and 1.

At block 10410, the quantum computer 104 may evolve the initial Hamiltonian 132 into the target Hamiltonian 134. Evolving the initial Hamiltonian 132 involves slowly switching "off" the initial Hamiltonian 132 and turning "on" the target Hamiltonian 134, based on the evolution rate 136. Although the goal of the evolution is to move from the initial Hamiltonian 132 to the target Hamiltonian 134 without leaving the ground state, in most cases, the system does leave the ground state due to system noise and Landau-Zener transitions. In a quantum annealing approach, dissipation and quantum tunneling are relied upon to return the system to a lower-energy state, or the ground state, if the system does leave the ground state.

During the evolution process, the system wavefunction extends over different local minima in the search space, and quantum fluctuations allow the algorithm to tunnel through barriers, thus settling into lower-energy states. The probability of tunneling depends on the strength of a transverse field in the annealing Hamiltonian. The strength of the transverse field (e.g., an electro-magnetic field) can be varied to adjust the probability of tunneling. When set to allow for a high tunneling probability, the algorithm is more likely to travel further in the problem space, which means that it is more likely to tunnel past a local minimum, but may also tunnel away from the desired global minimum. When configured for a lower tunneling probability, the algorithm may travel shorter distances in the problem space and be more likely to settle into a local minimum, also causing the algorithm to miss the global minimum. Thus, the probability of tunneling may be set on a case-by-case basis, depending on the configuration of the problem landscape (i.e., the search space).

After the initial Hamiltonian 132 is evolved into the target Hamiltonian 134, the states of the qubits should settle to a minimum value (i.e., either a local minimum or the global minimum). The settled qubit state represents the location in the search space that minimized the scoring function, and hence represents the protein configuration determined by the quantum algorithm to optimize the protein for the specified properties encompassed by the scoring function. Therefore, at block 412 the measurement unit 318 measures the states of the qubits, and at block 414, the quantum computer 104 returns the corresponding location in the search space as the answer to the problem as part of the classical output 304.

Figure 5:
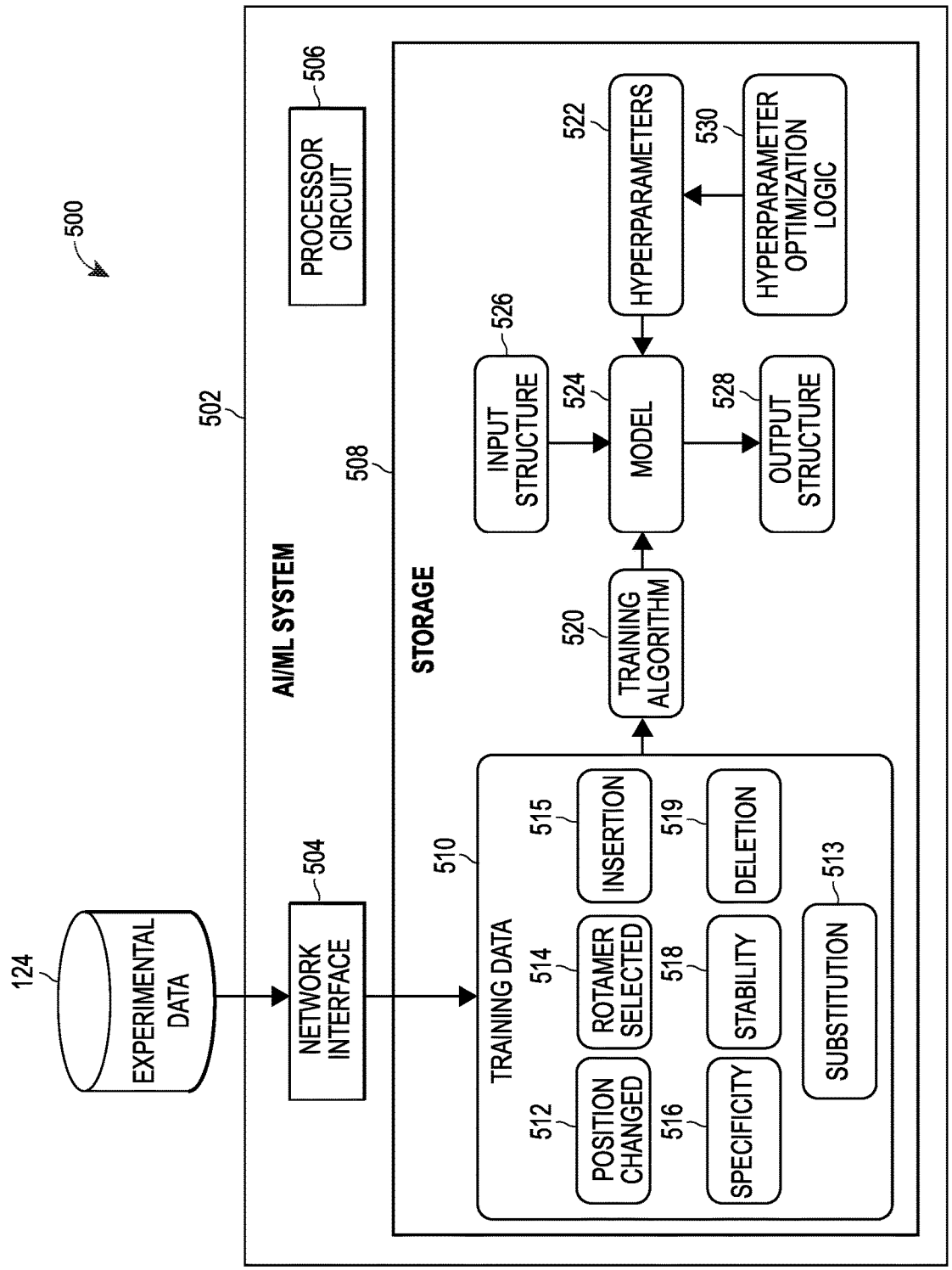
FIG. 5 illustrates an exemplary artificial intelligence/machine learning (AI/ML) system suitable for use with exemplary embodiments.

In addition to applying a quantum computer to more efficiently perform the search, artificial intelligence/machine learning (AI/ML) may be applied to learn relationships between the positions and/or amino acid modifications, additions, and/or deletions selected for adjustment, the rotamers applied at each position, and different protein structures and/or sequences, and the resulting changes in the properties for optimization 114. FIG. 5 is a block diagram of an AI/ML environment 500 suitable for applying AI/ML for performing protein design. As described herein, an AI algorithm or method may include one or more of machine learning, deep learning, reinforcement learning, or another AI algorithm or paradigm.

The AI/ML environment 500 may include an AI/ML System 502, such as a classical or quantum computing device that applies an AI/ML algorithm to learn relationships between the above-noted protein parameters. For example, the learned relationships between protein parameters may include a relationship between a protein sequence and protein properties, between a protein structure and protein properties, between a mutation of a protein and the resultant protein properties, and/or between the initial protein sequence, amino acid modifications, and rotamers and the resultant protein properties.

The AI/ML System 502 may make use of experimental data 124 returned by an experimental apparatus 108 as mutated proteins are tested. In some cases, the experimental data 124 may include pre-existing experimental data from databases, libraries, repositories, etc. The experimental data 124 may include an identification of a protein being tested, and measurements of the properties of the protein, potentially including measurements for the properties for optimization 114. The experimental data 124 may be collocated with the AI/ML System 502 (e.g., stored in a Storage 508 of the AI/ML System 502), may be remote from the AI/ML System 502 and accessed via a Network Interface 504, or may be a combination of local and remote data.

Training Data 510 may include the experimental data 124 returned from experimental apparatuses and the Training Data 510 may be supplemented by data learned by modeling and simulating proteins in software, and by parsing scientific and academic literature for information about sequence-function and structure-function relationships.

As noted above, the AI/ML System 502 may include a Storage 508, which may include a hard drive, solid state storage, and/or random access memory. The storage may store the Training Data 510, which may compare different test results to identify which position and/or amino acid modification was selected for adjustment in a test of a protein (i.e., a Position Changed 512, Substitution 513, Insertion 515, and/or Deletion 519), which rotamer was used at a changed position of the protein (i.e., a Rotamer Selected 514), and the measurements of the properties that resulted from the changes/mutations to the protein. In one example, the measurements of the properties may include the Specificity 516 and/or the Stability 518, solubility, expressibility, activity of the resulting protein, although other properties may be measured depending on the application.

The Training Data 510 may be applied to train a model 524. Depending on the particular application, different types of models 524 may be suitable for use. For instance, in the depicted example, an artificial neural network (ANN) may be particularly well-suited to learning associations between protein structures, positions, amino acid substitutions, amino acid insertions, amino acid deletions, and rotamers that gave rise to particular values for the properties of interest. Similarity and metric distance learning may also be well-suited to this particular type of task, although one of ordinary skill in the art will recognize that different types of models 524 may be used, depending on the designers goals, the resources available (e.g., classical or quantum computational resources), the amount of input data available, etc.

Any suitable Training Algorithm 520 may be used to train the model 524. Nonetheless, the example depicted in FIG. 5 may be particularly well-suited to a supervised training algorithm or reinforcement learning. For a supervised training algorithm, the AI/ML System 502 may apply the Position Changed 512, amino acid substitution selected 513, and Rotamer Selected 514 as a protein configuration in input data, to which resulting protein properties may be mapped to learn associations between the input data and the protein properties. The properties may be used as labels for the protein configuration. In a reinforcement learning scenario, the protein configuration may be adjusted by the model 524 in real time, and evaluated by another model that simulates the performance of the adjusted protein, or the protein configuration may be evaluated by synthesizing and producing the proteins, and carrying out experimental validations of the proteins. The AI/ML System 502 may attempt to maximize some or all, or a weighted combination, of the protein properties.

The Training Algorithm 520 may be applied using a Processor Circuit 506, which may include suitable hardware processing resources that operate on the logic and structures in the Storage 508. The Training Algorithm 520 and/or the development of the trained model 524 may be at least partially dependent on model Hyperparameters 522; in exemplary embodiments, the model Hyperparameters 522 may be automatically selected based on Hyperparameter Optimization logic 530, which may include any known hyperparameter optimization techniques as appropriate to the model 524 selected and the Training Algorithm 520 to be used.

The model 524 may be re-trained over time, in order to accommodate new knowledge and data about proteins and to incorporate data from further experiments performed.

In some embodiments, some of the Training Data 510 may be used to initially train the model 524, and some may be held back as a validation subset. The portion of the Training Data 510 not including the validation subset may be used to train the model 524, whereas the validation subset may be held back and used to test the trained model 524 to verify that the model 524 is able to generalize its predictions to new data.

Once the model 524 is trained, it may be applied, by the Processor Circuit 506, to new input data. The new input data may include current protein design problems (i.e., protein parameters to be optimized, target proteins, and binding agents, etc.) The new input data to the model 524 may be formatted according to a predefined input data structure 526 minoring the way that the Training Data 510 was provided to the model 524. The input data structure 526 may include an encoded sequence and/or structure information. The model 524 may generate an output data structure 528 which may be, for example, a prediction of protein structures, positions, amino acid modifications, and/or rotamer libraries most likely to impact targeted protein properties, or which protein features not to modify, and/or predicted properties, functions, or characteristics of the protein.

The output data structure 528 may be provided to the protein design pipeline 200 as a recommendation for protein structures, positions, amino acid modification, and rotamer libraries to be operated upon. In some embodiments, the output data structure 528 may provide a score or rank for those structures, positions, amino acid modifications, and rotamer libraries as described above.

The above description pertains to a particular kind of AI/ML System 502, which applies supervised learning techniques given available training data with input/result pairs. However, the present invention is not limited to use with a specific AI/ML paradigm, and other types of AI/ML techniques may be used. For example, in some embodiments the AI/ML System 502 may apply reinforcement learning, recommending protein changes to a user in the protein design pipeline 200 and observing how those changes affect the protein properties. From the information acquired by reinforcement learning, the AI/ML System 502 may learn a policy or set of rules defining which changes can be employed to affect which properties. Other AI/ML techniques, such as evolutionary algorithms, are also contemplated for use with the protein design pipeline 200.

The components and features of the devices described above may be implemented using any combination of discrete circuitry, application specific integrated circuits (ASICs), logic gates and/or single chip architectures. Further, the features of the devices may be implemented using microcontrollers, programmable logic arrays and/or microprocessors or any combination of the foregoing where suitably appropriate. It is noted that hardware, firmware and/or software elements may be collectively or individually referred to herein as "logic" or "circuit."

It will be appreciated that the exemplary devices shown in the block diagrams described above may represent one functionally descriptive example of many potential implementations. Accordingly, division, omission or inclusion of block functions depicted in the accompanying figures does not infer that the hardware components, circuits, software and/or elements for implementing these functions would be necessarily divided, omitted, or included in embodiments.

At least one computer-readable storage medium may include instructions that, when executed, cause a system to perform any of the computer-implemented methods described herein.

Some embodiments may be described using the expression "one embodiment" or "an embodiment" along with their derivatives. These terms mean that a particular feature, structure, or characteristic described in connection with the embodiment is included in at least one embodiment. The appearances of the phrase "in one embodiment" in various places in the specification are not necessarily all referring to the same embodiment. Moreover, unless otherwise noted the features described above are recognized to be usable together in any combination. Thus, any features discussed separately may be employed in combination with each other unless it is noted that the features are incompatible with each other.

With general reference to notations and nomenclature used herein, the detailed descriptions herein may be presented in terms of program procedures executed on a computer or network of computers. These procedural descriptions and representations are used by those skilled in the art to most effectively convey the substance of their work to others skilled in the art.

A procedure is here, and generally, conceived to be a self-consistent sequence of operations leading to a desired result. These operations are those requiring physical manipulations of physical quantities. Usually, though not necessarily, these quantities take the form of electrical, magnetic or optical signals capable of being stored, transferred, combined, compared, and otherwise manipulated. It proves convenient at times, principally for reasons of common usage, to refer to these signals as bits, qbits, qubits, values, elements, symbols, characters, terms, numbers, or the like. It should be noted, however, that all of these and similar terms are to be associated with the appropriate physical quantities and are merely convenient labels applied to those quantities.

Further, the manipulations performed are often referred to in terms, such as adding or comparing, which are commonly associated with mental operations performed by a human operator. No such capability of a human operator is necessary, or desirable in most cases, in any of the operations described herein, which form part of one or more embodiments. Rather, the operations are machine operations. Useful machines for performing operations of various embodiments include general purpose digital computers or similar devices.

Some embodiments may be described using the expression "coupled" and "connected" along with their derivatives. These terms are not necessarily intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Various embodiments also relate to apparatus or systems for performing these operations. This apparatus may be specially constructed for the required purpose or it may comprise a general purpose computer as selectively activated or reconfigured by a computer program stored in the computer. The procedures presented herein are not inherently related to a particular computer or other apparatus. Various general purpose machines may be used with programs written in accordance with the teachings herein, or it may prove convenient to construct more specialized apparatus to perform the required method steps. The required structure for a variety of these machines will appear from the description given.

It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment. In the appended claims, the terms "including" and "in which" are used as the plain-English equivalents of the respective terms "comprising" and "wherein," respectively. Moreover, the terms "first," "second," "third," and so forth, are used merely as labels, and are not intended to impose numerical requirements on their objects.

What has been described above includes examples of the disclosed architecture. It is, of course, not possible to describe every conceivable combination of components and/or methodologies, but one of ordinary skill in the art may recognize that many further combinations and permutations are possible. Accordingly, the novel architecture is intended to embrace all such alterations, modifications and variations that fall within the spirit and scope of the appended claims.

What is claimed is:

1. A computer-implemented method comprising:
   determining, by a processor, a protein sequence for optimization based on a protein property for optimization via an artificial intelligence or machine learning algorithm;
   providing, to the processor, the protein sequence for optimization;
   providing, to the processor, a protein structure having the protein sequence for optimization;
   providing, to the processor, the protein property for optimization;
   defining a scoring function based on the protein property for optimization;
   providing, to the processor, at least one of:
      a position in the protein sequence to be subjected to modification, or an amino acid to be substituted for the amino acid occurring at the position, inserted at the position, or deleted from the position, or
      a rotamer library to be searched for a target rotamer to be applied to one or more positions in the protein sequence;
   determining, by the processor, a search space based on the at least one of the position, amino acid substitution, amino acid insertion, amino acid deletion, or rotamer from the rotamer library;
   searching the search space using a quantum computing algorithm based on the scoring function, the searching comprising identifying at least one of a point mutation to the protein sequence or a combination of mutations to the protein sequence;

providing an output state of the quantum computing algorithm, the output state indicative of an optimized protein sequence of an optimized protein, the optimized protein sequence being optimized according to the scoring function based on the protein property for optimization;

experimentally testing the optimized protein to generate experimental data, the experimental data measuring one or more properties of the optimized protein, the one or more properties including at least one of:

the stability of the protein in terms of thermostability, pH stability, solvent stability, stability to other excipients, and/or stability in application;

expressibility;

solubility;

efficacy;

charge distribution;

protein folding;

activity;

specificity in terms of bond, group, substrate, stereo-specificity, and/or co-factor;

reversibility;

enzyme kinetics;

substrate inhibition;

product inhibition;

resistance to protease degradation;

gain-of-new function;

the affinity of the protein to the binding agent; or the specificity of the protein binding to similar binding partners, and providing the experimental data to the artificial intelligence or machine learning algorithm to train the artificial intelligence or machine learning algorithm to recognize a relationship between a sequence or structure of the optimized protein and the one or more properties measured by the experimental data.

2. The method of claim 1, further comprising:

providing, to the processor, a predefined binding partner of interest, and wherein providing the protein having the protein sequence for optimization comprises applying a computer-based model based on a structure or amino acid sequence of the binding partner of interest, or optimizing a binding partner for the selected protein during the searching.

3. The method of claim 1, further comprising:

testing the optimized protein for the protein property for optimization;

generating experimental data from the testing; and applying an artificial intelligence method to the experimental data to learn an association between a configuration of the optimized protein sequence and the protein property for optimization, the configuration comprising a two- or three-dimensional protein structure, an amino acid sequence, a DNA sequence that encodes the protein, or parts of a two- or three-dimensional protein structure, in particular a catalytic domain, or one or more domains of a protein.

4. The method of claim 3, wherein the artificial intelligence method comprises a machine learning method.

5. The method of claim 3, further comprising providing, based on the learned association, a protein sequence, a position, an amino acid substitution, an amino acid deletion, an amino acid insertion, or a rotamer library for consideration for the search space.

6. The method of claim 1, further comprising excluding a position, an amino acid substitution, an amino acid deletion, an amino acid insertion, or a rotamer library from the search space based on available quantum computing hardware.

7. The method of claim 1, wherein the quantum computing algorithm is a quantum annealing algorithm configured to search the search space for the optimized protein based on a target Hamiltonian determined from the scoring function.

8. The method of claim 1, wherein the quantum computing algorithm is one of a quantum-inspired algorithm, digital annealing algorithm, gate-based quantum algorithm, quantum simulation algorithm, or a quantum-inspired optimization.

9. The method of claim 1, wherein the quantum computing algorithm comprises one of a Quantum Approximate Optimization Algorithm, Grover Adaptive Search, adiabatic quantum computing, a quantum least squares fitting, quantum semidefinite programming, a quantum combinatorial optimization, a quantum-inspired stochastic regressions, a quantum-inspired evolutionary algorithm, quantum Monte Carlo quantum annealing, a simulated quantum annealing, quantum simulated annealing, or a quantum simulation with a variational quantum eigensolver.

10. The method of claim 1, wherein providing the protein comprises identifying a starting protein based on the protein property for optimization via computer-based modeling of the starting protein.

11. The method of claim 1, wherein the protein sequence for optimization includes an amino acid or a DNA sequence.

12. The method of claim 1, further comprising providing, to the processor, multiple target rotamers to be applied to a plurality of positions in the protein sequence.

13. The method of claim 1, further comprising providing, to the processor, a plurality of positions in the protein sequence to be subjected to modification, or a plurality of amino acids to be substituted for the amino acids occurring at the positions, inserted at the positions, or deleted from the positions.

14. The method of claim 1, wherein the output state of the quantum computing algorithm is indicative of a plurality of optimized proteins, and further comprising:

ranking, by the processor, each optimized protein of the plurality of optimized proteins;

determining, by the processor, a subset of the ranked plurality of optimized proteins; and further performing an optimization of a protein of the subset of the ranked plurality of optimized proteins.

15. The method of claim 14, wherein further performing an optimization of the protein comprises performing an optimization according to a quantum computing paradigm.

16. The method of claim 14, wherein further performing an optimization of the protein comprises performing an optimization by a classical computing system.

* * * * *